(12) United States Patent
Kenyon

(10) Patent No.: US 6,553,254 B1
(45) Date of Patent: Apr. 22, 2003

(54) COMBINATION OF NON-LIVING-SOURCE PHYSICAL ENERGY AND LIVING-SOURCE CHEMICAL ENERGY TO MAXIMIZE THE SALVAGE OF ATP

(76) Inventor: Keith E. Kenyon, 14435 Hamlin St., #C, Van Nuys, CA (US) 91401

( * ) Notice: Subject to any disclaimer, the term of this patent is extended or adjusted under 35 U.S.C. 154(b) by 0 days.

(21) Appl. No.: 09/545,121

(22) Filed: Apr. 7, 2000

(51) Int. Cl.[7] .................................................. A61N 1/30
(52) U.S. Cl. .............................. 604/20; 514/23; 606/27
(58) Field of Search ...................... 604/19, 20; 514/23; 606/27, 28, 32, 33

(56) References Cited

U.S. PATENT DOCUMENTS 4,719,201 A * 1/1988 Foker .......................... 514/23
4,871,718 A * 10/1989 Carniglia ...................... 514/23
6,159,942 A * 12/2000 St. Cyr et al. ................. 514/23
6,218,366 B1 * 4/2001 St. Cyr et al. ................. 514/23

* cited by examiner

Primary Examiner—Gregory L. Huson
Assistant Examiner—Tuan Nguyen

(57) ABSTRACT

A method of combining two energy-facilitating units for a therapeutic purpose, the first being a non-living-source physical energy device that employs such physical energy to be applied to a local area, and the second is a solitary chemical that employs living-source bioenergy to cells that are the target of the physical unit which combination renders increased intracellular energy to better effect healing by better salvaging and producing ATP.

20 Claims, 1 Drawing Sheet

COMBINATION OF NON-LIVING-SOURCE PHYSICAL ENERGY AND LIVING-SOURCE CHEMICAL ENERGY TO MAXIMIZE THE SALVAGE OF ATP

FIELD OF THE INVENTION

This application is in the field of therapeutics using an essential sugar, D-ribose, to energize cells that are being subjected to outside energy by physical devices designed to bring energy into the body.

RELATED APPLICATIONS

This patent application is related to patent application Ser. No. 09/263,071, entitled "A Method Enabling Magnetic Fields to Interact with Single Electrons in the Body in Order for Them to Experience and Exert a Force so as to Reduce Their Energy", patent application Ser. No. 09/354,434, entitled "The Use of Magnetic Fields to Improve the Taste of Water and Sugar by the Proposed Reason of Changing Free Electrons", and patent application Ser. No. 09/504,805, "The Use of D-Ribose to Improve Cellular Hypoxia and to Better Absorb Medicaments and Neutriceuticals".

BACKGROUND OF THE INVENTION

It is common knowledge that many drugs work one with another, synergistically, either to enhance an action or to enhance or cause a bad effect that would not have happened if the two drugs were not taken at the same general time. There is a carry over to this in the case of energy. The human body is subject to two types of energy. The first is the energy that enables life directly to exist. It comes from food, which is a living source of energy and enables us to function. Basically it is chemical energy that comes from the chemicals in food that are subjected to enzymatic action to strip electrons and pool them in the mitochondria for further chemical action to make nucleotides, especially ATP (adenosine tri phosphate). The fruits of this energy can be used by one person upon another by direct contact. Therefore, this constructive energy can work within the body itself and also be utilized by one person upon another for a therapeutic, as well as social, purpose. This is the branch of energy therapy that uses energy sources made by living cells. When it is applied to a body that is enduring a disease or disability by one person's energy being placed mechanically upon another, it has a general connotation of touch therapy, whereupon, the living energy that comes from one person's muscle cells is used to help another person therapeutically. It includes simple acupressure, chiropractic, massage therapy, and even faith healing when hands are applied. These forms of energy can be described as living-source energy.

On the other hand, all energy that is used upon the body is not generated from living cells. Some energy comes from the use of therapeutic devices. This will be called physical energy in contradistinction to living or chemical energy derived from nutrition. Like chemical energy, physical energy also can be constructive when used for therapeutic purposes, but it can also be destructive and still be used for therapeutic purposes. Thus, it can be divided into a number of subtypes, which are divided into many different devices in which non-living or non-cellular energy penetrates through the layers underneath the skin. Such energy includes devices that transmit electromagnetic radiation all the way from infrared heat to gamma radiation, light being included. Even hot packs can transmit heat into layers underneath the skin itself. Cold-transmission called cryotherapy is in this classification also, in which instruments employing frozen carbon dioxide or liquid nitrogen are the principal devices. Non-living-source physical energy also includes sonography, especially ultrasound devices such as therapeutic ultrasound. It even includes vibratory devices which utilize electromagnetic energy in the form of AC current on a device that makes an electromagnet move quickly in opposite directions to cause a vibration on the skin which enables non-living-source physical electrical energy to become non-living-source mechanical energy and by direct contact this mechanical energy is conducted through the various layers below the skin ultimately to stimulate key structures. All of these kinds of energy are derived from electromagnetic sources or the use of electromagnetic devices, even ultrasound which needs electricity to enable a transducer to make the sound waves. The same is true for cryogenic devices which require refrigeration to make liquid nitrogen, etc. None are derived by living cells that remain alive during the energy-generating process, because the process would kill them. For example, burning wood to heat up a hot pack or to use the heat from burning petroleum to enable a turbine to revolve to make electricity came from what were living cells once but are no longer alive.

All of this non-living-source energy originally comes either from the sun, other cosmic radiation, or radioactive material on earth. To be utilized as therapeutic energy it must be harnessed by man-made instruments, apparatuses and devices that mostly harness the energy from the sun in various ways. Specifically in this disclosure we are going to describe outside, non-living-source energy, used in devices that promote healing so have a therapeutic use as opposed to a diagnostic use. An Xray puts energy into the body but it is mostly used for diagnostic purposes. On the other hand, Xrays can be utilized therapeutically for a few diseases such as certain kinds of cancer. The same is true with magnetic flux. When used in an MRI it is for diagnostic purposes but when a permanent magnet has been energized by an electric field, it can put flux into the body for a therapeutic purposes as can an electromagnet. Of course, a very common type of diagnostic instrument uses ultrasound, but ultrasound was originally used clinically as a therapeutic device. All of these energy devices, whether they be transcutaneous electrical nerve stimulating (TENS) devices, ultrasound, vibratory instruments, magnets, or a laser stimulating acupuncture points, stimulate nerves, muscles and other organs to stimulate the production of neurotransmitters such as endorphins and serotonin. However, cells that need such stimulation are usually relatively hypoxic, and the stimulation, which some say improves circulation, also goes to stimulate the salvage of ATP to render the cells less hypoxic so as to be better able to be healed.

For the first time there is now a biochemical way to make the cells less hypoxic that does not directly come from food and can bypass much of the tedious natural way to combat hypoxia by increasing intracellular energy. For the first time, this makes it possible to have a synergistic energy combination to promote healing using a living source of energy generated from inside the body and a non-living source of energy generated from outside the body.

This invention is designed to overcome the deficiencies of previous applications and inventions using a combination of non-living-source physical energy and living-source chemical energy to increase the salvage rate of ATP by stimulating the normal enzymatic process and also to increase the production of ATP even more by chemically shortcutting the process, so that synergistically more ATP than expected will be produced and salvaged than either physical stimulation or chemical action could yield if one were used without the other.

SUMMARY OF THE INVENTION

This disclosure is about therapeutic devices that employ non-living-source physical energy for a treatment, which is simultaneously augmented by chemical energy from living cells and tissue, and organs made from them, to increase the effectiveness of the treatment. This invention was not possible until D-ribose became available for general distribution. Except for ribose there is no carbon atom that can fulfill the chemical part of this disclosure rapidly and actually augment or increase the final stage of the energy that ordinarily comes from food and is deposited into the mitochondria as activated electrons extracted from the food via the respiratory electron channel. that make their way to the mitochondria and molecular oxygen. This compound is not consumed as a food. Rather it is more like the way a synthetic drug has a molecular action, and its molecular structure is the reason it works. Ribose lends its molecular structure to forming ATP (adenosine tri phosphate) more quickly at a time when quickness is very desirable and even life-saving. With respect to the natural process, it does not start out as ribose. Rather it undergoes a tedious enzymatic pathway to be formed starting out as glucose. When de novo ribose is administered, it shortcuts this process and can form ATP much faster. As a result, the ordinary salvage of ATP can be enhanced by direct stimulation by the application of the non-living-source of physical energy. Then with de novo D-ribose, a short cut to produce even more ATP can-be provided. The combination will result in the potentiation of more rapid healing of structures targeted by the physical energy device than would be the case without the de novo D-ribose.

Although for decades this compound, D-ribose, has been known to be an essential energy sugar and building block sugar, being a direct part of all genetic material as well as ATP, and being an indirect part of connective tissue and glycogen, unlike its precursor in the body, glucose, it's not available in usable quantities as a free molecule in nature. It's not a vitamin because it's synthesized from glucose in the body, nor can it be extracted from the body like hormones. Free ribose must be manufactured by biological means or by chemical means outside the body. Furthermore, when introduced to the body in its pentose state, it changes the metabolism of ATP to eliminate a number of enzymatic reactions. Thus, it shortcuts the process whereby ATP is made or salvaged in the body, and therefore speeds up the normal pathway that intracellular energy is made in the mitochondria. Therefore, it is not a nutrient from the technical point of view but a drug, because like a drug it interacts and alters the way the normal metabolism or chemical action of a cellular process is being conducted in the body when it is introduced.

As a consequence, ribose actually is a drug that has just recently been introduced, so specific discrete uses have patentability if they combine to make different kinds of energy work together to, among other benefits, combat the hypoxia of cells for better healing. The main present use for ribose is in the recovery of skeletal muscle cells that have been rendered hypoxic as a result of intense exercise and the recovery of cardiac muscle cells that have been rendered hypoxic by ischemia. In patent application No. Ser. 09/504, 805 ribose is used with medicaments, which include drugs and herbs used as medicaments, and other nutrients to increase their absorption when the cell is maximally energized by the addition of ribose. Thus, ribose is a chemical that can increase the amount of living energy that a hypoxic cell needs to reduce the hypoxia.

A number of conditions render cells in the body hypoxic. A list of most of them includes: trauma, ischemia, anemia, inefficient respiration, excessive cold or heat, vascular disruption (atherosclerosis), poisons, pollutants, infective agents, a side effect of certain medication, allergic reactions, and degenerative and genetic diseases.

For some of these conditions, the use of outside non-living-source physical energy can enable the body to stimulate ATP salvage and thereby help the immune system heal, and render the targeted cells less hypoxic so that they can heal or function better. If a chemical means were administered before the physical means were utilized so that both could be working synergistically, making increased ATP available by stimulation of salvage and direct production together, the amount of ATP generated could be more than either method of treatment alone could produce. This result could be ascertained by annecdotal methods to describe the improvement when both were used.

The simplest kind of physical energy applied comes from moderate heat and TENS therapy. This therapy is directed to cells that are more hypoxic than they normally would be because of the disease or condition. When this kind of energy therapy is too intense, it can render the already hypoxic cells temporarily even more hypoxic than they would ordinarily be, and in this case the chemical energy is more needed than otherwise. Such physical therapy is done in order to increase circulation, which it can do, but the principal result of the stimulation is to stimulate the salvage of ATP. When de novo D-ribose is given with the energy therapy, before, during and after the stimulation, it can enhance the salvage of ATP by bypassing the tedious slow glycolitic process. Unless it is too intense or severe, this kind of physical energy coming from energy devices like a heating pad, a TENS device, a magnet or a laser is constructive.

However, when desired, some of these devices can intentionally put destructive energy into the body to remove a tumor, stop bleeding, or even alter a tissue. This degree of energy takes the process a step beyond what was called intense therapy above. In this case the treatment is to remove or alter a tissue, and the physical energy device destroys tissue so does not stimulate ATP salvage directly. It renders cells adjacent to the area being treated, hypoxic, and the need for D-ribose is even greater in this case, although the synergy then is indirect. In this case destruction of some of the cells stimulates the salvage of ATP by other cells. However, the destruction will render the adjacent cells and the immune system with even more need to receive ATP, because they must engage in direct healing of the site itself Pure radiation therapy such as X rays promote cellular hypoxia which needs cellular energy for relief so from that point of view salvage of ATP is stimulated. Most of these kind of devices have a hand-held applicator that touches or virtually touches body tissues. The therapeutic use of such devices, with or without a hand-held applicator, always deliberately heats tissue sufficiently to destroy it or freezes it sufficiently to destroy it. The use of such devices is considered to be surgical, but it differs from conventional multi-step surgery in that only the one instrument or device is used on the tissue and with an outside energy supply. However, it can be used in open or laprascopic incisions along with other instruments. However, of itself, it is a one-step procedure using destructive energy from a single device to remove the condition entirely including stopping bleeding or rendering tissue into a superior state such as corneal laser applications. However, the procedure stimulates the normal salvage of ATP. As with all destructive procedures, adjacent normal tissue cannot help but be involved to varying degrees. This invention rests upon the principle that if a source of constructive living-source chemical energy could be administered as another step along with the destructive energy as a step, the accompanying non-desirable destruction could heal faster as a result of the increased ATP thus generated so can render the target area to be returned to health faster.

When such destructive heat or cold devices are used, the tissues or substances needed to be destroyed are eliminated, but surrounding tissues have been traumatized and rendered hypoxic so that their mitochondria must go to work to salvage as much ATP as possible to energize the healing. Here we want to utilize a combination of two discrete, solitary energy-facilitating units, one non-living-source physical energy and the other living-source bioenergy, each to join the other in accomplishing better, a single therapeutic purpose rendered by the physical energy.

Summing up, this purpose in part is to utilize constructive energy to stimulate healing in part by increasing the salvage of ATP to reduce hypoxia of the affected cells and in part destructive heat or cold in order to remove an unwanted or undesirable structure in the body, stop bleeding, or not to remove anything but to alter a cellular structure in the body. The first unit is a non-consumable physical unit that puts non-living-source physical energy inside the body and its cells, the use of which one way or the other stimulates the salvage of ATP. The second unit is a consumable chemical unit that enables increased intracellullar chemical or bioenergy to get inside the body's cells to shortcut and thereby increase the direct production of ATP. The first unit consists of different kinds of solitary instruments and apparatuses and the second unit is a chemical.

When the physical device destroys tissue, quick healing becomes important The original such destructive instrument was a piece of metal thrust into a fire to get enough heat to cauterize a wound. When electricity became available electric currents were introduced with sufficient energy to destroy undesirable tissue or substances. The electric cautery was the first sophisticated outcome of utilizing concentrated electromagnetic radiation to target heat to a much more narrow area than was the case with the original device. The advent of light amplification by stimulated emission of radiation, its achronym being the "laser", brought the narrow targeting area of the targeted tissue by destructive heat to a new much smaller area. With the laser, minimal damage to adjacent normal tissue with minimal scarring was discovered and now is expected. Nevertheless, no mechanical thing is perfect and neither is the laser even in the hands of the best technician treating the best kind of patient. When a crude cautery is used, it is, of course, desirable to have maximum speed of healing with minimum scarring. However, this does not always happen, but it is not expected to in every case. Thus, there is more forgiveness for bad results. However, with the laser every means to maximize the speed of healing and minimize the scarring is desirable and necessary because it is expected by the public. Cryotherapy is not used nearly as much as laser therapy and is not nearly as discrete in minimizing the target area, but it needs the same healing action.

With respect to devices that employ constructive energy, a hot pack was the original device. However, with the advent of harnessing various types of electromagnetic radiation, many devices, including TENS devices, infra red radiation, laser devices, electric heat pads and permanent magnets can be combined with ribose to potentiate the entire process of achieving quickly more ATP.

The foregoing discussion about the physical part of our two units, unit one, should make it understandable that if a chemical part could speed healing and keep scarring minimal by providing more intracellular energy to hypoxic cells resulting from the condition being treated, it would be a useful combination that is not at present utilized with this understanding, even though means to do so has recently become available. Thus, when this biochemical means to augment maximum speed of healing keep scarring minimal became available, once the public knew about it, it would be expected by the public in laser therapy in particular, to make the results of such therapy even better, because of the high expectation the public has for laser therapy. Furthermore, it would also be desirable to use unit two in conjunction with all kinds of therapeutic non-living-source physical energy devices.

With respect to unit two the only nutrient, nutriceutical, drug or herb that can shortcut ATP salvage and by that help traumatized tissue heal faster by bringing more internal constructive energy to the site of the external destructive energy is D-ribose, which prior to this application has not been used deliberately with laser or cryo-therapy. D-ribose is a key nutrient, the "D" of the DNA of every cell, part of the "A" of ATP, as well as a main precursor for the mucopolysaccharides of connective tissue and cartilage and, of course, is in the DNA of the skin cells themselves and the skin's mitochondria as well as that of deeper tissues including endothelial cells. This nutrient can be used with a variety of dose timing. It can be started the day before a laser skin treatment, continued on the day of treatment and again on the following day, or it can be used for a shorter period or a much longer period. In any case, many times healing will improve noticeably using ribose over not using ribose at all. The body including the skin is a biochemical factory. ATP is the product of the energy factories (mitochondria) in the cell and ribose is the fuel.

Of course, every precaution to limit the risk of burning normal adjacent tissue to the targeted site should be taken. In the case of using destructive heat to target melanin in hair follicles, even a laser with high specificity for melanin can inadvertently cause damage to the skin surrounding the hair follicle. Cooling techniques such as employing sapphire, which has excellent thermal characteristics and operates as a heat sink in removing heat from the epidermis can be used. In addition, compression techniques for the area being heated, so as to form good thermal contact, collapse blood vessels to prevent their competition for the radiation, force the hair down and bring follicle roots closer to the surface, can be employed. Nevertheless, healing must still take place and damage can ensue with the treatment, for which the faster and better it heals, the better it is for both therapist and patient.

Physical energy treatment devices are complete devices in and of themselves, however they can be used in conjunction with other devices including with tracking devices to situate their probes properly. They can also be used as part of the instrumentation required in invasive surgery including laproscopic. Cautery is a common fulgerating device so the burn must be healed. The same is true if a laser were used for that purpose during a surgical procedure. When the laser is to be used as a surgical cutting instrument rather than as a fulgerating one, the issue is the same. Healing of the tissues so burned as a result of a cutting objective is still required, and the faster and better it happens, the better for all involved. When eye lasers that put out much less total energy are used, minimizing side effects by enabling the mitochondria of the cells of the eye to be more energized, still is desirable. With respect to the use of any kind of therapeutic laser, what ribose does is make a good thing better.

The features of the present invention which are believed to be novel are set forth with particularity in the appended claims. The present invention, both as to its organization and the manner of operation, together with the further objects and advantages thereof, may be best understood by reference to the following exemplary and non-limiting detailed description of the invention, taken in conjunction with the following drawings, wherein;

DETAILED DESCRIPTIONS OF THE PREFERRED EMBODIMENT

Figure 1:
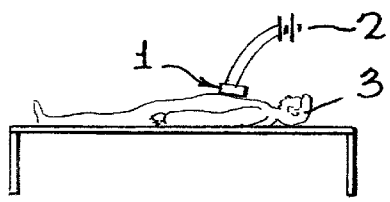
FIG. 1 A view of a non-living-source physical energy device being applied to a patient.
Figure 2:
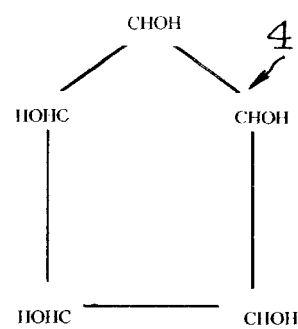
FIG. 2 The chemical formula of the pentose sugar, D-ribose.

This disclosure is for the purpose of combining unit one, one of a number of acceptable solitary physical devices employing non-living-source physical energy shown as 1 in FIG. 1 utilizing this outside source of energy 2 for the purpose as one use of converting said energy to destructive heat (or cold if it is cryotherapy) that can be targeted to a relatively small part of the body of a patient 3 for the doctor or technician, not shown, to perform a therapeutic purpose using the applicator part of unit one, not shown, with unit two, shown in FIG. 2, a carbon compound 4 essential to the body, that when provided can increase the intracellular bioenergy of cells, in order to minimize the hypoxia to the cells that result from the trauma to the cells, and maximize healing both with respect to the time it takes to achieve and the quality of the healing achieved. The procedure being described involves the first step of providing a patient 3 with a suitable amount of D-ribose 4, such as 2 grams for a single dose, for oral ingestion or parentally given if that is desired, immediately before the procedure. Then in step two procuring a physical energy source usually an electrical outlet 2, and in step three procuring said physical energy device 1 that converts the incoming energy into locally destructive heat energy for targeting an intended structure or site in the body. The laser is most widely used such device. In step four the area around the site to be targeted is cleaned to remove infective material that could get into the wound soon to be inflicted, and in step five, physical cooling means, not shown, are provided to the area surrounding the target site to minimize heat damage on normal tissue and in step six the handpiece delivering the locally destructive heat is applied to the target tissue. In order to further maximize the benefit of the step employing the D ribose 4 it can be extended in use to the day or days before the actual treatment and in step seven continued after the treatment at least one time but preferably for a number of days or continuously if the energy benefits of ribose are to be continued. The value of using the D-ribose is many fold but minimizing the antioxidants resulting from making the traumatized cells hypoxic is paramount.

Superoxide is formed when leaked "energy" electrons from the mitochondrial electron pools act upon "leaked" oxygen. This is the start of the free-radical formation, which when used for good, enables leukocytes (for example, neutrophils providing respiratory bursts) to destroy pathogens, etc. and when used for bad, destroys the mitochondria and as a result, the cells. Ascorbate provides the needed electrons to enable itself and other antioxidants such as superoxide dismutase and glutathione peroxidase to scavenge superoxide, peroxides, ozone and other oxidants as the first step to counteract hypoxia. So that ascorbic acid does not form the toxic oxidant, dehydroascorbic acid, the electrons must be returned to it from the mitochondrial pool.

Figure 3:
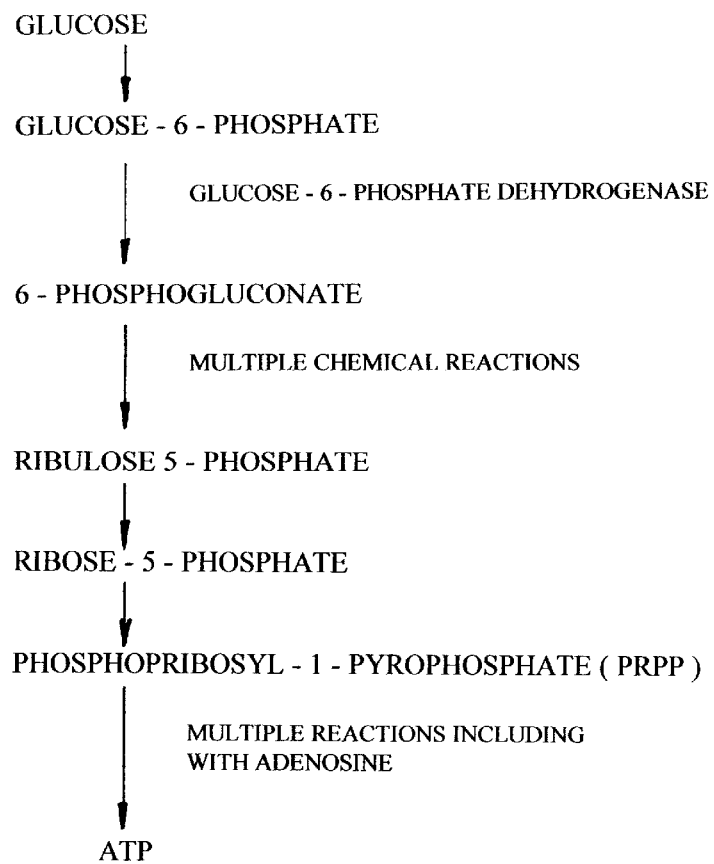
FIG. 3 The formation of ATP without the administration of de novo ribose.
Figure 4:
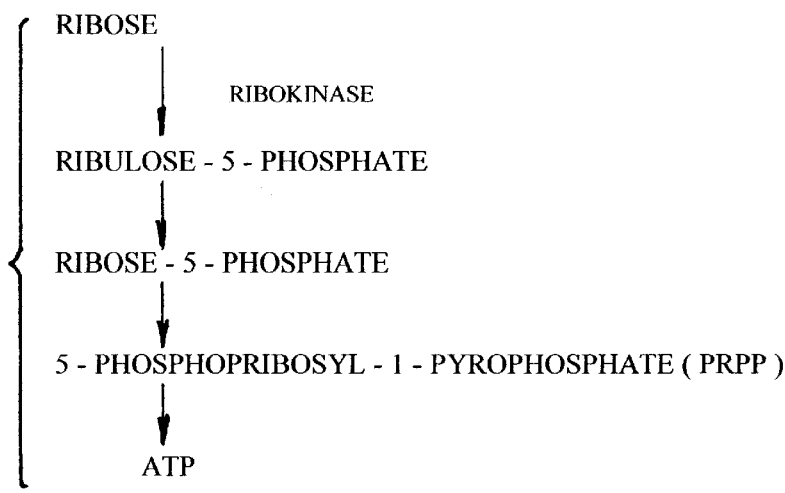
FIG. 4 The ribose shortcut to produce ATP.

Hypoxic mitochondria, cannot do this well. It is the result of an insufficient ability for them to produce intracellular energy that an attack (trauma or an illness from virtually any cause) on the body causes. FIG. 3 shows the normal much more complex way that ATP is formed or salvaged as a result of the normal pathway. Notice the number of chemical reactions that take place. This is the reason why salvaging ATP is a tedious procedure and takes more time than is available in serious cases and delays healing more than it should in others. FIG. 4 shows ribose shortcutting the normal chain to ATP. It makes the body better able to provide enough nucleotides (ATP) through the respiratory electron transfer chain (enzymatic dehydrogenase to the cytochrome oxidative complex yielding oxidative phosphorylated nucleotides, like ATP) to prevent excess electron leakage. Thus, de novo D-ribose can provide the patient a chemical shortcut to make ATP faster with the chemical shortcut that administering de novo D-ribose can achieve. De novo D-ribose can bypass much of the pentose phosphate pathway via glucose, to form the near-end product of ATP, PRPP (5-phosphoribosyl-1-pyrophospate), directly. De novo D-ribose bypasses most of the slow glycolytic (fermentation) salvage route for immediate oxidative phosphorylation and more intracellular energy when the body needs it to make even more sure—that when laser treatment is being applied the best possible result can be realized. We thus have a simple solution to minimize the effects of hypoxia. Give the cells more energy, but keep the oxidant population low by minimizing electron leakage. We need D-ribose for immediate and continuous restoration of the electron pool in the mitochondria. D-ribose undergoing the procedure extra intracellular energy for better ability to scavenge the excess superoxides formed when cells are hypoxic as a result of the treatment. When the oxygen content of a cell is low, it impairs the flow of electrons through the respiratory electron transfer chain ATP is needed. A second use for unit one when less energy is employed is to stimulate ATP salvage without the destruction of cells but with de novo D ribose potentiating ATP production.

Figure 5:
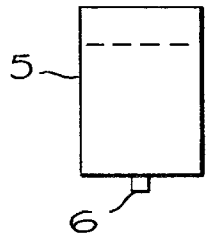
FIG. 5 A permanent magnet attached to a ribose container.

Finally FIG. 5 shows a container 5 of D-ribose which has a permanent magnet 6 either inside the container or attached to an outside wall including the bottom. Among other things, the magnet will render the ribose sweeter which is important because ribose is only a slightly sweet sugar and making it sweeter enables purer ribose to be used in a powder or lozenge While particular embodiments of the present invention have been shown and described, it will be obvious to those skilled in the art that changes and modifications may be made without departing from my invention in its broader aspects of a method to utilize de novo D ribose with therapeutic devices employing energy in order to facilitate the formation of increased intracellular energy in order to facilitate more rapid and complete healing.

I claim:

1. A method of employing both an amount of D-ribose and a device employing non-living source physical energy, together, for a therapeutic purpose in a treatment procedure, comprising the steps of:
   a. obtaining at least one gram of D-ribose and giving said D-ribose to a patient by oral or parenteral means prior to said treatment procedure and then;
   b. obtaining a source of outside physical energy to enable said device employing said outside energy to become operational and then;
   c. making available said physical energy device for application to remove or repair said tissue and then;
   d. directing said device toward the targeted tissue and applying said energy to remove or repair said tissue and then;
   e. giving more of said D-ribose to the patient being treated after said treatment procedure.

2. The method according to claim 1 in which the device employing non-living source physical energy emits electromagnetic radiation selectively from infra-red to gamma rays.

3. The method according to claim 1 in which the device employing non-living source physical energy is a laser.

4. The method according to claim 1 in which the device employing non-living source physical energy is an electrocautery.

5. The method according to claim 1 in which the device employing non-living source physical energy is a cryogenic device.

6. The method according to claim 1 in which the device employing non-living source physical energy is an icepack.

7. The method according to claim 1 in which the device employing non-living source physical energy is a transcutaneous electrical nerve stimulating (TENS) device.

8. The method according to claim 1 in which the device employing non-living source physical energy is a heating pad.

9. The method according to claim 1 in which the device employing non-living source physical energy is an ultrasonic therapeutic device.

10. The method according to claim 1 in which the device employing non-living source physical energy is an infra-red emitting device for the purpose of administering heat.

11. The method according to claim 1 in which the device employing non-living source physical energy is a vibrator.

12. The method according to claim 1 in which the device employing non-living source physical energy is an ultraviolet light source.

13. The method according to claim 1 in which the device employing non-living source physical energy employs X-rays.

14. The method according to claim 1 in which the device employing non-living source physical energy employs radioactive isotopes.

15. The method according to claim 1 in which said D-ribose can be given more than one day prior to the treatment procedure.

16. The method according to claim 1 in which D-ribose can be given more than one day after the treatment procedure.

17. The method according to claim 1 in which a container holding the D-ribose has a permanent magnet adjacent to said container.

18. The method according to claim 17 in which said container holding the D-ribose does not have a permanent magnet adjacent to said container.

19. The method according to claim 1 in which said D-ribose becomes a nucleotide in the body.

20. The method according to claim 19 in which one of the nucleotides is ATP.

* * * * *